United States Patent [19]

Coppola

[11] 4,261,894
[45] Apr. 14, 1981

[54] PROCESS FOR THE PREPARATION OF OPTIONALLY SUBSTITUTED 2,3-INDOLINEDIONES

[75] Inventor: Gary M. Coppola, Budd Lake, N.J.

[73] Assignee: Sandoz, Inc., E. Hanover, N.J.

[21] Appl. No.: 106,406

[22] Filed: Dec. 26, 1979

Related U.S. Application Data

[62] Division of Ser. No. 966,200, Dec. 4, 1978, Pat. No. 4,212,804.

[51] Int. Cl.$^3$ ............................................. C07D 209/40
[52] U.S. Cl. ................................................. 260/326.11 R
[58] Field of Search ................................. 260/326.11 R

[56] References Cited

U.S. PATENT DOCUMENTS

| 3,132,151 | 5/1964 | Bortnick et al. | 260/326.11 R |
| 3,984,563 | 10/1976 | Winters et al. | 260/326.11 R |

OTHER PUBLICATIONS

S. Kadin et al., Chem. Abstracts 87:151986y (1977), A Convenient Synthesis of 2-amino-4-hydroxyquinolines.
H. Aurich et al., Chem. Ber. 1972, 105(7), 2389-2397.

*Primary Examiner*—Donald G. Daus
*Assistant Examiner*—M. C. Eakin
*Attorney, Agent, or Firm*—Gerald D. Sharkin; Richard E. Vila; Joseph J. Borovian

[57] ABSTRACT

An improved process for the preparation of optionally substituted 2,3-indolinediones which are useful as intermediates in the preparation of compounds having pharmacological activity which comprises reacting a 3,1-benzoxazine with an alkali or alkaline earth metal cyanide or a tetra-($C_{1-4}$) alkylammonium cyanide to obtain a 2-imino-3-indolinone, which is then subjected to hydrolysis.

10 Claims, No Drawings

PROCESS FOR THE PREPARATION OF OPTIONALLY SUBSTITUTED 2,3-INDOLINEDIONES

This is a division of application Ser. No. 966,200, filed Dec. 4, 1978, now U.S. Pat. No. 4,212,804.

This invention relates to a new and more efficient process for the preparation of optionally substituted 2,3-indolinediones which are useful in the preparation of compounds having pharmacological activity.

More particularly, the process of the present invention involves the preparation of 2,3-indolinediones of the formula I:

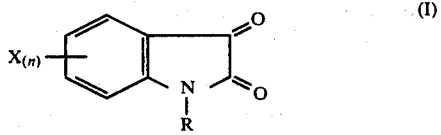

wherein
R is hydrogen; $C_{1-4}$ alkyl; $C_{3-6}$ alkenyl; $C_{3-6}$ alkynyl; unsubstituted phenyl; phenyl substituted by one or two substituents independently selected from $C_{1-4}$ alkyl; $C_{1-4}$ alkoxy, fluoro, chloro and bromo; unsubstituted benzyl; or benzyl substituted on the benzene ring by one or two substituents independently selected from $C_{1-4}$ alkyl, $C_{1-4}$ alkoxy, fluoro, chloro and bromo;

X is fluoro; chloro; bromo; $C_{1-4}$ alkyl; $C_{1-4}$ alkoxy; or nitro; or two adjacent X's together may also form methylenedioxy; and n is 0 or an integer 1 or 2, the two X's being the same or different when n is 2.

The 2,3-indolinediones of formula I are prepared by a two-step procedure involving in a first Step 1, the reaction of a 3,1-benzoxazine of formula II:

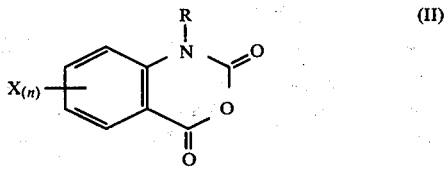

wherein R, X and n are as defined above, with an alkali or alkaline earth metal cyanide or a tetra-($C_{1-4}$)alkylammonium cyanide in a molar ratio of cyanide compound to a compound of formula II of about at least 1:1, to decarboxylate and 3,1-benzoxazine and obtain a 2-imino-3-indolinone of formula III:

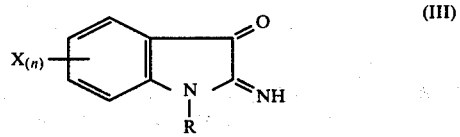

wherein R, X and n are as defined above, said 2-imino-3-indolinone of formula III then being subjected in Step 2 to hydrolysis to obtain the 2,3-indolinedione of formula I.

The molar ratio of cyanide compound to compound of formula II in the preparation of compounds of formula III is about at least 1:1. Although the reaction may be conducted in the presence of a large excess of the cyanide compound, i.e., in a molar ratio of cyanide compound to compound of formula II of 10:1, it is preferred that the reaction be conducted in about an equimolar ratio or in the presence of a slight excess (e.g., up to 10%) of the cyanide compound.

The preparation of compounds of formula III by the decarboxylation of compounds of formula II employing an alkali or alkaline earth metal cyanide may be carried out at temperatures in the range of from 80° to 140° C., preferably 90° to 120° C., and more preferably, at 100° C. Although the source of the cyanide ion may be any alkali or alkaline earth metal cyanide, the alkali metal cyanides are preferred, especially sodium and potassium cyanide. The decarboxylation is carried out in the presence of an organic solvent which is inert and adapted to dissolving the reactants and the product compound of formula III. Suitable solvents are known and available, and include by way of illustration, the liquid, di-lower alkyl amides of formic and acetic acids, preferably dimethylformamide. The resulting product of formula III may be isolated from the reaction of Step 1 by working up by conventional procedures.

The preparation of compounds of formula III by the decarboxylation of compounds of formula II employing a tetra-($C_{1-4}$) alkylammonium cyanide may be carried out at temperatures in the range of from 10° to 80° C., preferably 30° to 50° C., and more preferably, at 40° C. Although any tetra-($C_{1-4}$) alkylammonium cyanide may be employed, a tetra-($C_1$ or $C_2$) alkylammonium cyanide is preferred, more preferably, tetraethylammonium cyanide. The decarboxylation is carried out in the presence of an organic solvent which is inert and adapted to dissolving the reactants and the product compound of formula III. Suitable solvents are known and available and include by by way of illustration, the chlorinated hydrocarbons, preferably methylene chloride. The resulting product of formula III may be isolated from the reaction of Step 1 by working up by conventional techniques.

The preparation of compounds of formula I by Step 2 involving the hydrolysis of a compound of formula III is desirably effected under alkaline, neutral or acid conditions, preferably mild acidic conditions, suitably using hydrochloric or sulfuric acid, preferably hydrochloric acid. The hydrolysis may be carried out conveniently at a temperature of from −40° to 100° C., preferably at a temperature of from 10° to 30° C. The resulting product of formula I may be isolated from the reaction mixture of Step 2 by working up by established procedures.

The 3,1-benzoxazines of formula II employed as starting materials in Step 1 are either known and obtained by methods described in the literature, or where not known, may be obtained by methods analogous to those described in the literature.

The 2-imino-3-indolinones of formula III, which are produced by the reaction of Step 1, are novel compounds and also form part of this invention.

The compounds of formula I are known and, as previously indicated, are valuable intermediates in that they are useful in preparing compounds having pharmacological properties. The compound of formula I and a process for converting them into compounds having pharmacological activity are disclosed in U.S. Pat. No. 4,020,179, U.S. Pat. No. 3,509,149, British Pat. No. 975,357 and Sci. Pharm. 38(2), 98–106 (1970).

Among the compounds for which the process of this invention is useful are compounds of formula I and the novel intermediate compounds of formula III wherein:

(1) R is hydrogen, $C_{1-4}$ alkyl, $C_{3-6}$ alkenyl, $C_{3-6}$ alkynyl, unsubstituted phenyl or unsubstituted benzyl, and n is 0;

(2) R is $C_{1-4}$ alkyl, X is $C_{1-4}$ alkyl, fluoro, chloro or bromo, and n is 1; and (3) R is hydrogen, X is fluoro, chloro or bromo, and n is 1.

The following examples are for purposes of illustration only and are not intended to in any way limit the scope of the invention.

EXAMPLE 1

1-methyl-2,3-indolinedione

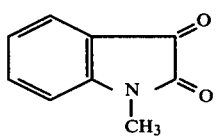

Step 1: Preparation of 2-imino-1-methyl-3-indolinone

To a suspension of 1.3 g. (0.021 moles) of pulverized potassium cyanide in 75 ml. of dimethylformamide (distilled over calcium hydride) at 100° C. is added dropwise, over a period of 15 minutes, a solution containing 3.6 g (0.02 moles) of 1-methyl-2H-3,1-benzoxazine-2,4(1H)-dione in 35 ml. of dimethylformamide (distilled over calcium hydride), after which time the reaction mixture is stirred at 100° C. for an additional 5 minutes. The resultant mixture is then poured into cold water and extracted into three 250 ml. portions of ether. After drying the organic phase over sodium sulfate, the excess solvent is removed and the resultant precipitate is filtered, washed with ether and dried in vacuo to yield 2-imino-1-methyl-3-indolinone, m.p.99°–120° C. (Yield: 49%).

Step 2: Preparation of 1-methyl-2,3-indolinedione

A suspension of 100 mg. of 2-imino-1-methyl-3-indolinone in 5 ml. of 2N-hydrochloric acid is warmed slightly on a steam bath and allowed to stand at ambient temperature for one hour, after which time the resultant precipitate is filtered, washed with water and dried in vacuo to yield 1-methyl-2,3-indolinedione, m.p. 134°–136° C.

EXAMPLE 2

Following essentially the procedure of Example 1, and using in place of 1-methyl-2H,-3,1-benzoxazine-2,4(1H)-dione in Step 1, an equivalent amount of:

(a) 6,7-dimethoxy-1-methyl-2H-3,1-benzoxazine-2,4-(1)-dione, (b) 1-(2-propynyl)-2H-3,1-benzoxazine-2,4-(1H)-dione, (c) 1-(2-propenyl)-2H-3,1-benzoxazine-2,4-(1H)-dione, or (d) 1-benzyl-2H-3,1-benzoxazine-2,4-(1H)-dione, there is obtained (a) 6,7-dimethoxy-2-imino-1-methyl-3-indolinone, m.p. 134°–138° C. (Yield: 14%), (b) 2-imino-1-(2-propynyl)-3-indolinone, m.p. 121°–123° C. (Yield: 50%), (c) 2-imino-1-(2-propenyl)-3-indolinone, an oil (Yield: 77%), and (d) 1-benzyl-2-imino-3-indolinone, m.p. 81°–83° C. (Yield: 66%), respectively.

EXAMPLE 3

Following essentially the procedure of Example 1, and using in place of 2-imino-1-methyl-3-indolinone in Step 2, an equivalent amount of each of the compounds obtained in Example 2, there is obtained (a) 6,7-dimethoxy-1-methyl-2,3-indolinedione, (b) 1-(2-propynyl)-2,3-indolinedione, m.p. 153°–155° C. (Yield: 85%), (c) 1-(2-propenyl)-2,3-indolinedione, m.p. 82°–84° C. (Yield: 65%), and (d) 1-benzyl-2,3-indolinedione, m.p. 127°–128° C., respectively.

EXAMPLE 4

1-methyl-2,3-indolinedione

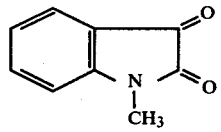

Step 1: Preparation of 2-imino-1-methyl-3-indolinone 500 mg. of 1-methyl-2H-3,1-benzoxazine-2,4(1H)-dione and 500 mg. of tetraethylammonium cyanide is added to 15 ml. of methylene chloride and the reaction mixture is refluxed for 3½ hours, after which time the reaction mixture is washed successively with water and a saturated sodium chloride solution. After drying the organic phase over sodium sulfate, the excess solvent is removed to yield crude, oily 2-imino-1-methyl-3-indolinone, which can be purified to yield the desired compound in crystalline form.

Step 2: Preparation of 1-methyl-2,3-indolinedione

Following essentially the procedure of Step 2 in Example 1, the 2-imino-1-methyl-3-indoline prepared in Step 1 is hydrolyzed to yield 1-methyl-2,3-indolinedione.

What is claimed is:

1. A process for the preparation of a 2-imino-3-indolinone of the formula,

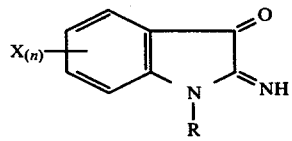

wherein R is hydrogen; $C_{1-4}$ alkyl; $C_{3-6}$ alkenyl; $C_{3-6}$ alkynyl; unsubstituted phenyl; phenyl substituted by one or two substituents independently selected from $C_{1-4}$ alkyl, $C_{1-4}$ alkoxy, fluoro, chloro and bromo, unsubstituted benzyl; or benzyl substituted on the benzene ring by one or two substituents independently selected from $C_{1-4}$ alkyl, $C_{1-4}$ alkoxy, fluoro, chloro and bromo;

X is fluoro; chloro; bromo; $C_{1-4}$ alkyl; $C_{1-4}$ alkoxy; or nitro; or two adjacent X's together may also form methylenedioxy; and n is 0 or an integer 1 or 2, the two X's being the same or different when n is 2, which comprises reacting a 3,1-benzoxazine of the formula,

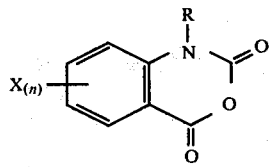

wherein R, X and n are as defined above, with an alkali or alkaline earth metal cyanide or a tetra-($C_{1-4}$) alkylammonium cyanide in an equimolar ratio or in the presence of a slight excess of the cyanide compound, to decarboxylate said 3,1-benzoxazine and obtain said 2-imino-3-indolinone.

2. The process according to claim 1 in which the 3,1-benzoxazine is reacted with an alkali metal cyanide at a temperature of from about 80° to 140° C.

3. The process according to claim 2 wherein the 3,1-benzoxazine is reacted with an alkali metal cyanide at a temperature of from about 90° to 120° C.

4. The process according to claim 2 wherein the alkali metal cyanide is potassium cyanide.

5. The process according to claim 1 in which the 3,1-benzoxazine is reacted with a tetra($C_{1-4}$) alkylammonium cyanide at a temperature of from about 10° to 80° C.

6. The process according to claim 5 wherein the 3,1-benzoxazine is reacted with a tetra-($C_{1-4}$) alkylammonium cyanide at a temperature of from about 30° to 50° C.

7. The process according to claim 5 wherein the tetra-($C_{1-4}$) alkylammonium cyanide is tetraethylammonium cyanide.

8. The process according to claim 1 in which the 3,1-benzoxazine is reacted with potassium cyanide in an equimolar ratio or in the presence of a slight excess of potassium cyanide at a temperature of 100° C., to decarboxylate said 3,1-benzoxazine and obtain a 2-imino-3-indolinone.

9. The process according to claim 1 in which the 3,1-benzoxazine is reacted with tetraethylammonium cyanide in an equimolar ratio in the presence of a slight excess of tetraethylammonium cyanide at a temperature of 40° C., to decarboxylate said 3,1-benzoxazine and obtain a 2-imino-3-indolinone.

10. A compound of the formula,

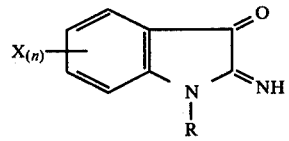

wherein
R is hydrogen; $C_{1-4}$ alkyl; $C_{3-6}$ alkenyl; $C_{3-6}$ alkynyl; unsubstituted phenyl; phenyl substituted by one or two substituents independently selected from $C_{1-4}$ alkyl, $C_{1-4}$ alkoxy, fluoro, chloro and bromo; unsubstituted benzyl; or benzyl substituted on the benzene ring by one or two substituents independently selected from $C_{1-4}$ alkyl, $C_{1-4}$ alkoxy, fluoro, chloro and bromo;
X is fluoro; chloro; bromo; $C_{1-4}$ alkyl; $C_{1-4}$ alkoxy; or nitro; or two adjacent X's together may also form methylenedioxy; and
n is 0 or an integer 1 or 2, the two X's being the same or different when n is 2.

* * * * *

UNITED STATES PATENT AND TRADEMARK OFFICE
CERTIFICATE OF CORRECTION

PATENT NO. : 4,261,894
DATED : April 14, 1981
INVENTOR(S) : Gary M. Coppola

It is certified that error appears in the above-identified patent and that said Letters Patent is hereby corrected as shown below:

Title page, left-hand column, Item [54]; change the title to --PROCESS FOR THE PREPARATION OF OPTIONALLY SUBSTITUTED 2-IMINO-3-INDOLINONES--.

At the top of Column 1; change the title to --PROCESS FOR THE PREPARATION OF OPTIONALLY SUBSTITUTED 2-IMINO-3-INDOLINONES--.

Column 1, line 52; after "decarboxylate"; change "and" to --said--.

Column 3, line 40; after "m.p.", change "99°-120°" to --99°-102°C--.

Column 4, line 45; before "prepared", change "2-imino-1-methyl-3-indoline" to --2-imino-1-methyl-3-indolinone--.

Column 4, Claim 1, line 4 beneath the structural formula; after "bromo", change the comma to a semicolon.

Column 6, Claim 9, line 3; after "ratio", insert --or--.

Signed and Sealed this

Twenty-fifth Day of January 1983

[SEAL]

Attest:

GERALD J. MOSSINGHOFF

Attesting Officer   Commissioner of Patents and Trademarks